(12) United States Patent
Pai

(10) Patent No.: US 8,060,180 B2
(45) Date of Patent: Nov. 15, 2011

(54) MULTI-ECHO MAGNETIC RESONANCE IMAGING METHOD AND SYSTEM

(75) Inventor: Vinay M. Pai, New York, NY (US)

(73) Assignee: New York University, New York, NY (US)

(*) Notice: Subject to any disclaimer, the term of this patent is extended or adjusted under 35 U.S.C. 154(b) by 1673 days.

(21) Appl. No.: 11/334,178

(22) Filed: Jan. 17, 2006

(65) Prior Publication Data

US 2006/0161060 A1 Jul. 20, 2006

Related U.S. Application Data

(60) Provisional application No. 60/643,798, filed on Jan. 14, 2005.

(51) Int. Cl.
*A61B 5/05* (2006.01)

(52) U.S. Cl. ........ 600/410; 600/419; 600/420; 324/307; 324/309

(58) Field of Classification Search .......... 600/410, 600/419, 420; 324/307, 309
See application file for complete search history.

(56) References Cited

U.S. PATENT DOCUMENTS

| | | | | |
|---|---|---|---|---|
| 6,078,175 | A * | 6/2000 | Foo | 324/306 |
| 6,806,709 | B2 * | 10/2004 | Markl et al. | 324/309 |
| 2003/0152516 | A1 * | 8/2003 | Driehuys et al. | 424/9.3 |
| 2003/0184291 | A1 * | 10/2003 | Rehwald et al. | 324/307 |
| 2005/0001619 | A1 * | 1/2005 | Kiefer | 324/309 |

OTHER PUBLICATIONS

Herzka et al., "Multishot EPI-SSFP in the Heart", Apr. 2002, Magn Reson Med, pp. 1-20.*
Elizabeth Henderson et al., "A Fast 3D Look-Locker Method for Volumetric $T_1$ Mapping", Magnetic Resonance Imaging, vol. 17, No. 8, pp. 1163-1171, 1999.
Ken Nkongchu et al., "An Improved 3-D Look-Locker Imaging Method for $T_1$ Parameter Estimation", Magnetic Resonance Imaging, vol. 23, pp. 801-807, 2005.
D.C. Look et al., "Time Saving in Measurement of NMR and EPR Relaxation Times", The Review of Scientific Instruments, vol. 41, No. 2, Feb. 1970, pp. 250-251.
George P. Chatzimavroudis et al., "Evaluation of the Precision of Magnetic Resonance Phase Velocity Mapping for Blood Flow Measurements", Journal of Cardiovascular Magnetic Resonance, vol. 3, No. 1, pp. 11-19, 2001.
Daniel A. Herzka et al., "Multishot EPI-SSFP in the Heart", Magnetic Resonance in Medicine, vol. 47, pp. 655-664, 2002.

(Continued)

*Primary Examiner* — Brian Casler
*Assistant Examiner* — Christopher Cook
(74) *Attorney, Agent, or Firm* — Dorsey & Whitney LLP

(57) ABSTRACT

Exemplary method, systems and arrangements can be provided for creating a high-resolution magnetic resonance image ("MRI") or obtaining other information of a target. For example, radio-frequency ("RF") pulses can be transmitted toward the target by a RF transmitter of a MRI apparatus. In response, multiple echoes corresponding to each pulse may be received from the target. Data from each of the echoes can be assigned to a single line of k-space of a distinct image, and stored in memory of the apparatus. An image of the target, velocity data and/or acceleration data associated with a target can be generated as a function of the data. In one exemplary embodiment, the data from different echoes can be assigned to the same k-space line and to different cardiac phases. The exemplary embodiments of the present disclosure can be utilized for the heart or for any other anatomical organ or region of interest.

33 Claims, 10 Drawing Sheets

OTHER PUBLICATIONS

J.H. Holmes et al., "Respiratory-Gated 3D Hybrid PR for Hyperpolarized He-3 Ventilation Imaging in Asthma-like Small Animal Model", Proc. Intl. Soc. Mag. Reson. Med. vol. 13, p. 1823, 2005.

M. Markl et al., "Balanced Phase-Contrast Steady-State Free Precession (PC-SSFP): A Novel Technique for Velocity Encoding by Gradient Inversion", Magnetic Resonance in Medicine, vol. 49, pp. 945-952, 2003.

Krishna S. Nayak et al., "Real-Time Color Flow MRI", Magnetic Resonance in Medicine, vol. 43, pp. 251-258, 2000.

Charles X. Kim et al., "Moderated Poster Presentation I", Taylor & Francis et al. pp. 91-99, Friday, Jan. 21, 2005.

Brian Saam et al., "Rapid Imaging of Hyperpolarized Gas Using EPI", Magnetic Resonance in Medicine, vol. 42, pp. 507-514, 1999.

Michael Salerno et al., "Dynamic Spiral MRI of Pulmonary Gas Flow Using Hyperpolarized $^3$He: Preliminary Studies in Healthy and Diseased Lungs", Magnetic Resonance in Medicine, vol. 46, pp. 667-677, 2001.

Richard B. Thompson et al., "High Temporal Resolution Phase Contrast MRI with Multiecho Acquisitions", Magnetic Resonance in Medicine, vol. 47, pp. 499-512, 2002.

Martin Blaimer et al., "Smash, Sense, Pils, Grappa, How to Choose the Optimal Method", Top Magn Reson Imaging, vol. 15, No. 4, pp. 223-236, Aug. 2004.

* cited by examiner

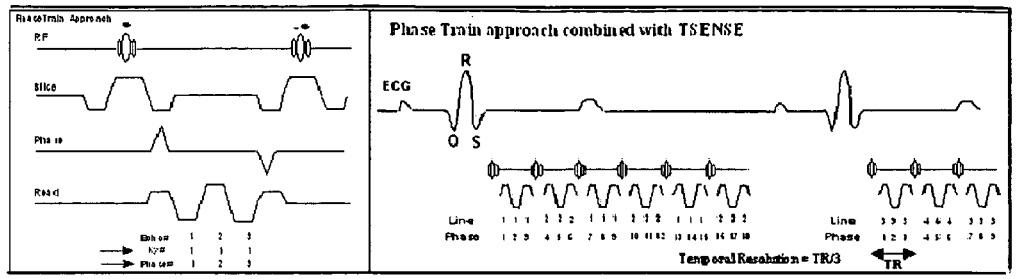
Figure 7(a)    Figure 7(b)
 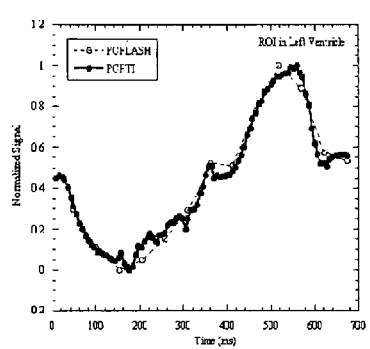 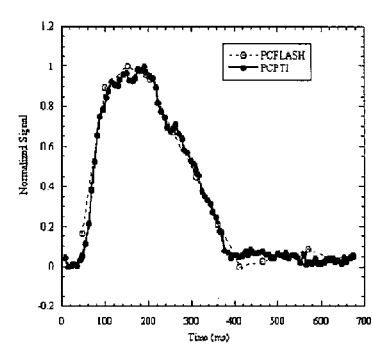
Figure 8(a)    Figure 8(b)    Figure 8(c)
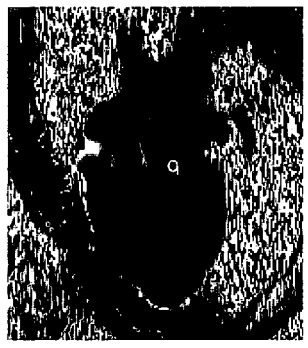 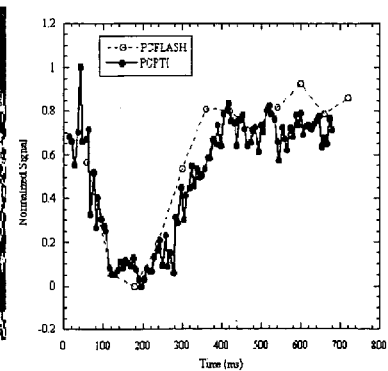 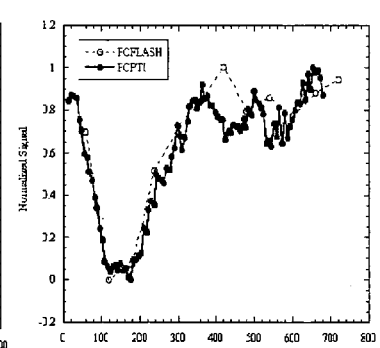
Figure 9(a)    Figure 9(b)    Figure 9(c)

| HB | 0 | 1 | 2 | 3 |
|---|---|---|---|---|
| Trigger | X | | | |
| Inversion Pulse | XX | | | |
| MEM | MEM MEM MEM MEM MEM MEM MEM MEM MEM | | | |

Figure 15

| HB | 0 | 1 | 2 | 3 |
|---|---|---|---|---|
| Trigger | X | X | X | X |
| Inversion Pulse | XX | XX | XX | XX |
| MEM | MEM1 | MEM2 | MEM3 | MEM4 |

Figure 16

| HB | 0 | 1 to n-1 | n | n+1 to 2n-1 |
|---|---|---|---|---|
| Trigger | X | | X | |
| Inversion Pulse | XX | | XX | |
| MEM | | MEM1 MEM1......MEM1 | | MEM2 MEM2.........MEM2 |

Figure 17

MULTI-ECHO MAGNETIC RESONANCE IMAGING METHOD AND SYSTEM

CROSS-REFERENCE TO RELATED APPLICATION(S)

This application is based upon and claims the benefit of priority from U.S. Patent Application Ser. No. 60/643,798, filed Jan. 14, 2005, the entire disclosure of which is incorporated herein by reference.

FIELD OF INVENTION

The present invention relates to magnetic resonance imaging ("MRI"). More particularly, the present invention relates to method and system for generating MRI data using a multi-echo approach. The present invention also relates to methods and systems for increased temporal resolution or increased combinations of temporal and spatial resolution. The present invention further relates to methods and systems which are capable of imaging or characterizing flow dynamics with high temporal resolution including, without limitation, flow conditions in the heart or any organ of the body. The present invention still further relates to methods and systems which are capable of producing T1 maps, perfusion imaging or imaging any other magnetization-prepared techniques with a reduced time.

BACKGROUND INFORMATION

In the field of MRI and particularly in the field of cardiac MRI, a series of images may be acquired that have different slices of the target (e.g., the patient's heart) at different times (e.g., at different times during the cardiac cycle). Typically, the temporal resolution of each "cine" scan can be approximately 30-50 milliseconds, which is generally limited only by the patient's breath-hold duration, typically 5-25 seconds. This temporal resolution is sufficient for a number of MRI applications, such as a study of a general cardiac function. This resolution may be insufficient for other applications, such as a study of extremely rapid mechanical cardiac functions, for example, valve motion, mechanical activation maps, and evaluation of mechanical dyssynchrony, which is a key indicator for early stages of systolic contraction and diastolic expansion.

To improve temporal resolution, one conventional approach can use a multi-echo steady-state free precession ("MESSFP") technique which is known. The MESSFP technique permits temporal resolutions of approximately 5 milliseconds and acquisition of single-slice datasets in a single breath-hold scan. In this approach, each echo acquires data for a different line of frequency space (e.g., k-space), and all echoes in the train of echoes acquires data for the same cardiac phase. The MESSFP technique is phase-dependent, and requires a smooth transition from one line of k space to the next line of k space. For example, the phase referred to herein is the phase of the complex data, which can be labeled as a "complex" phase. MESSFP also requires a careful design to avoid "complex" phase-based ghosting artifacts, uses various magnetic field gradient schemes (e.g., flyback schemes, echo-shifting, etc.). These considerations limit the temporal resolution of the MESSFP technique to approximately 5 milliseconds, in a series of three (3) echoes.

Single echo SSFP (e.g., balanced or unbalanced SSFP) techniques allow for a temporal resolution of approximately 2.5 milliseconds, but suffer from certain problems. For example, single echo SSFP techniques require application of a large number of radio frequency ("RF") pulses into the patient's body, which is undesirable. Also, for sequences that involve magnetization preparation (e.g., magnetization tagging), application of a high number of RF pulses causes an early destruction of the magnetization preparations (i.e., the tags fade faster). This potentially limits the analysis of prepared datasets (i.e., tagged datasets) to a small fraction of the cardiac cycle.

MESSFP techniques are generally used in conjunction with parallel imaging techniques, such as time-adaptive sensitivity encoding ("TSENSE"), "complex" phased array approach to ghost elimination ("PAGE"), sensitivity encoding ("SENSE"), simultaneous acquisition of spatial harmonics ("SMASH") or Generalized Autocalibrating Partially Parallel Acquisitions ("GRAPPA"), to speed up data acquisition. The reconstruction based on this combination can be a lengthy process because each echo in the train of echoes (or echo-train) contributes to the same image, or cardiac phase, and it may not be easy to parallelize the reconstruction of the data acquired using this combination.

Magnetic resonance "complex" phase velocity mapping (PVM) using a "complex" phase contrast approach is a procedure that has been used clinically to measure blood flow (e.g., see G. P. Chatzimavroudis et al., "Evaluation of the precision of magnetic resonance phase velocity mapping for blood flow measurements," J Cardiovasc Magn. Reson. 2001; 3(1):11-9). However, conventional "complex" phase contrast (PC) magnetic resonance imaging may have a lower temporal resolution than corresponding magnitude imaging, due to the preference to acquire two differentially flow-encoded images for every PC image frame, in order to subtract out or remove non-motion-related "complex" phase changes.

Spiral "complex" phase contrast pulse sequences have been used (e.g., see K. S. Nayak et al., "Real-time color flow MRI," Magn Reson Med 2000; 43(2):251-8) to develop real-time color flow MRI. Since this approach is real-time, no breath-holding or gating is needed. In this approach, a sliding window reconstruction can be used to acquire the data. However, this approach can only yield temporal resolution of up to 60 msec (e.g., when used with single-shot spirals), with a corresponding spatial resolution of 4 mm.

The used of balanced steady-state free precession (b-SSFP) has been demonstrated (e.g. see M. Markl et al., "Balanced phase-contrast steady-state free precession (PC-SSFP): a novel technique for velocity encoding by gradient inversion," Magn Reson Med 2003; 49(5):945-52) to perform "complex" phase contrast imaging (PC-SSFP). b-SSFP sequences are attractive since they exhibit intrinsically higher signal-to-noise ratios (SNRs) than conventional imaging sequences. The publication by Markl, et al. demonstrates an approach to encode for flow without introducing any additional velocity encoding gradients, so as to keep the repetition time (TR) as short as in typical SSFP sequences. Instead, sensitivity is established to through-plane velocities by inverting (i.e., negating) all gradients along the slice-select direction. It was possible to adjust the velocity encoding sensitivity (Venc) by altering the first moments of the slice-select gradients. In order to avoid disturbing the SSFP steady state, they acquired different flow echoes in sequentially executed scans, each over several cardiac cycles, using separate steady-state preparation periods. Using this approach, it was possible to show that PC-SSFP exhibited a higher intrinsic SNR and consequently lower "complex" phase noise in measured velocities compared to conventional "complex" phase contrast (PC) scans. It was also demonstrated that PC-SSFP is less reliant on in-flow-dependent signal enhancement, and hence yields more uniform SNR and better depiction of vessel geometry throughout the cardiac cycle in structures with slow and/or pulsatile flow. Their acquisition, however, had a temporal resolution of only 58 ms.

The highest temporal resolution "complex" phase contrast MRI has been demonstrated (e.g., see R. B. Thompson et al., "High temporal resolution phase contrast MRI with multi-echo acquisitions," Magn Reson Med 2002; 47(3):499-512) by using a multiecho acquisition. In this publication, an improvement by a factor of 2 in the temporal resolution was achieved by acquiring the differentially flow-encoded images in separate breath-holds rather than interleaved within a single breath-hold. They also utilized the multiecho readout to acquire more views per unit time than is possible with the conventional PCMRI sequence. These changes allowed them to achieve a total improvement in temporal resolution by ~5 times over conventional PC imaging. They were able to achieve a temporal resolution of 11.2 ms and an in-plane spatial resolution of 2 mm×2 mm. Yet higher temporal resolution than that achieved to date is desirable which will allow the acquisition of very high resolution velocity data. This can be used, for example, for the evaluation of valvular function and flow mechanics. The present invention provides for finer detail of jets that may arise from regurgitation and/or stenosis. The present invention permits the highest temporal resolution velocity measurement with MRI than that which is known to have ever been recorded before.

Single-shot magnetic resonance imaging, in which the data corresponding to the entire image is acquired in a single instance, can generally be used to acquire snapshot images of physiologic processes. While echo-planar imaging (EPI) is one of the renowned examples of fast snapshot imaging, this technique may suffer from various artifacts, such as susceptibility, and $T_2$ or $T_2^*$ signal attenuation effects, which reduce its practical usefulness to select regions of the body, and to low spatial resolutions. One potential region where there is a preference for fast snapshot imaging is studying lung dynamics using hyperpolarized helium (3He) (or similar polarized or hyperpolarized gas) MRI. Due to the short $T2^*$ of 3He (approximately 12 ms), EPI is not a practical solution for clinically useful spatial resolutions (3 mm or less). While techniques such as spiral imaging have been developed for fast imaging, such techniques have to utilize sliding window approaches to achieve "high" temporal resolution. Beside the situation that spiral imaging may be nontrivial to reconstruct, the sliding window approach can lead to an averaging of the data over multiple time points, making it difficult to determine the true temporal resolution of the data. Segmented and multi-echo gradient recalled approaches have been developed to overcome some of the artifacts associated with conventional EPI techniques. These approaches acquire only a short echo train corresponding to a portion of the data representing the image after every RF pulse. This approach can enable data acquisition within $T2^*$ limits, may minimize the susceptibility artifact, and can allow higher spatial resolution to be achieved. However, this segmented approach can make it difficult to acquire data with the type of temporal resolution that is achieved with EPI.

High temporal resolution dynamical imaging of lungs using hyperpolarized gases such as 3He can be used for diagnosis of many pulmonary diseases. Different techniques have been developed to achieve this. For example, fast EPI has been developed to achieve temporal resolution of 40 ms (see, e.g., Saam et al., MRM. 1999; 42:507-514)) for matrix size 32×64. A projection reconstruction method (see, e.g., Holmes et al., Proc. ISMRM, Miami, 2005) provides a temporal resolution of 366 ms for matrix size 256×256. Interleaved spiral imaging can provide a temporal resolution of 3.4 ms for matrix size 128×128 using 24 interleaves and a sliding window technique for reconstruction (see e.g. Salerno et al., MRM 2001 46:667-677). However, spiral imaging can be cumbersome to implement and the sliding window reconstruction leads to time averaging of the signal. One of the major problems encountered in making accurate maps of T1 is the long time generally needed. For a good accuracy over a wide range of T1 values, multiple points of the T1 recovery curve should be sampled. If a conventional two-dimensional (2D) inversion-recovery spin-echo sequence is used, data acqisition for each slice can take a significant time (e.g., several hours). Several schemes have been developed for the rapid imaging of T1 in 2D in which multiple points on the recovery curve can be sampled. These techniques can include methods based on Look-Locker, snapshot-fast low-angle shot (snapshot—FLASH), inversion prepared echo planar imaging, and stimulated echo imaging.

SUMMARY OF EXEMPLARY EMBODIMENTS OF THE INVENTION

There exists a need to provide an improved magnetic resonance imaging method and system which overcomes at least some of the above-referenced deficiencies. Accordingly, at least this and other needs have been addressed by exemplary embodiments of the multi-echo imaging method and system according to the present invention.

Exemplary embodiments of the present invention may combine the advantages of the multi-echo gradient recalled EPI imaging and parallel imaging with the concept of the temporal resolution being governed by the time taken to reach the center of k-space. This combination can permits the snapshot imaging to be performed with high temporal resolution, and does not require the use of a sliding window reconstruction. Accordingly, the temporal resolution achieved in this exemplary manner can be closer to the actual resolution, rather than average. Since such resolution can be based on a Fourier approach to image acquisition, the image reconstruction is easier as compared to spiral imaging. In addition, exemplary embodiments of the present invention may be used to acquire high temporal resolution images using polarized gas or hyperpolarized gas. Such use may include without limitation lung imaging with hyperpolarized helium. For example, according to one exemplary embodiment of the present invention, cine imaging application where single-shot (e.g., the entire image data may be acquired in a single acquisition) can be utilized to improve temporal resolution. Further, the exemplary embodiments of the present invention may be used for perfusion imaging, fast T1 mapping or similar magnetization-prepared imaging techniques.

One such exemplary embodiment of the present invention can be directed to a method and system for generating an image, velocity data and/or acceleration data by forwarding a plurality of radio-frequency ("RF") pulses toward a target, and receiving a plurality of echoes associated with the plurality of pulses. Data from each of the echoes can be assigned to a single line of k-space and to multiple cardiac phases. Further, the image, velocity data and/or acceleration data of the target can be generated using the data.

In another exemplary embodiment of the present invention, a magnetic resonance imaging apparatus can be provided which may include a processor, an RF transmitter, and an RF receiver. The receiver and transmitter are in communication with the processor. The RF transmitter can preferably send a plurality of RF pulses toward a target, such as a cardiac region of a patient. The RF receiver can receive data from a plurality of echoes created by the pulses and sends the data to the processor. The processor may also assign data from the echoes to a single line in k-space and to multiple cardiac phases, and can generate an image and/or velocity data or acceleration data of the target using the data.

In yet another exemplary embodiment of the present invention, a magnetic resonance imaging ("MRI") apparatus can be provided, having a first arrangement which may be configured to transmit a plurality of radio-frequency ("RF") pulses toward a target; and a second arrangement may be configured to receive a plurality of echoes corresponding to the plurality of pulses. The apparatus can further include a third arrangement configured to assign data from each of the echoes of the echo train to a single line of k-space and to multiple cardiac phases, and a fourth arrangement configured to generate an image and/or velocity data or acceleration data of the target using the data.

In yet another embodiment of the present invention, a tangible, computer-readable medium can be provided having stored thereon computer-executable instructions for performing a method of creating a magnetic resonance image and/or velocity data or acceleration data. The medium includes a first set of instructions that sends a plurality of radio-frequency ("RF") pulses toward a target, a second set of instructions that assigns data from each of a plurality of echoes from associated with the RF pulses to a single line of k-space and to multiple cardiac phases, and a third set of instructions that generates an image and/or velocity data or acceleration data of the target using the data.

In yet another exemplary embodiment of the present invention, a method, system and processing arrangement can be provided for providing an image, velocity data and/or acceleration data by forwarding a plurality of radio-frequency ("RF") pulses toward a target, and receiving a plurality of echoes associated with the plurality of pulses. Data from each of the echoes can be acquired so that the echoes may reach a center of k-space at different time points. Further, the image, velocity data and/or acceleration data of the target may be generated using the data.

For example, according to still a further exemplary embodiment of the present invention, it is possible to provide an SSFP based multi-echo sequence that may allow an increased temporal resolution imaging. Such increased temporal resolution imaging may include, without limitation, cine imaging of the lungs with polarized gas or hyperpolarized gas. The hyperpolarized gas may include without limitation hyperpolarized helium or other hyperpolarized gasses.

According to still another exemplary embodiment of the present invention, a method, system and computer-readable medium are provided for obtaining information associated with a target. For example, a plurality of radio-frequency ("RF") pulses can be forwarded toward the target. A plurality of echoes associated with the pulses can be received, whereas at least one of the echoes can reach a center of k-space at a first point in time and at least further one of the echoes reaches the center of the k-space at a second point in time which is different than the first point. Further, an image of the target can be generated as a function of the data.

At least one of the exemplary embodiments of the present invention can provide faster and more accurate perfusion maps.

These and other objects, features and advantages of the present invention will become apparent upon reading the following detailed description of embodiments of the invention, when taken in conjunction with the appended claims.

BRIEF DESCRIPTION OF DRAWINGS

Further objects, features and advantages of the invention will become apparent from the following detailed description taken in conjunction with the accompanying figures showing illustrative embodiments of the invention, in which:

FIG. 7(a) is an exemplary application of a multi-echo phase train imaging. over a single repetition ("TR");

FIG. 7(b) is an exemplary application of multi-echo phase train imaging. over a over a cardiac cycle;

FIG. 8(a) is an exemplary application of a "complex" phase contrast with HF encoding to provide a PD image (with the regions of interest—"ROIs"—being in LV and PA);

FIG. 8(b) is a graph of an exemplary normalized LV velocity component in the HF direction generated using the exemplary application of FIG. 8(a);

FIG. 8(c) is a graph of an exemplary normalized PA velocity component in the HF direction generated using the exemplary application of FIG. 8(a);

FIG. 9(a) is an exemplary application of the "complex" phase contrast with LR encoding generating a PD image, with the ROIs being in LV and PA);

FIG. 9(b) is a graph of an exemplary normalized velocity LV component estimation by both sequences in the LR direction generated by the exemplary application of FIG. 9(a);

FIG. 9(c) is a graph of an exemplary normalized velocity PA component estimation by both sequences in the LR direction generated by the exemplary application of FIG. 9(a).

FIG. 15 is a table providing an exemplary implementation of an exemplary embodiments of the present invention which is independent from a cardiac cycle;

FIG. 16 is a table providing another exemplary implementation of an exemplary embodiments of the present invention which is dependent on the cardiac cycle;

FIG. 17 is a table providing yet another exemplary implementation of an exemplary embodiments of the present invention which is independent from the cardiac cycle, and which uses a multiMEM technique to improve a temporal resolution of inversion times imaged;

DETAILED DESCRIPTION OF THE EXEMPLARY EMBODIMENTS

First Exemplary Embodiments

Figure 1:
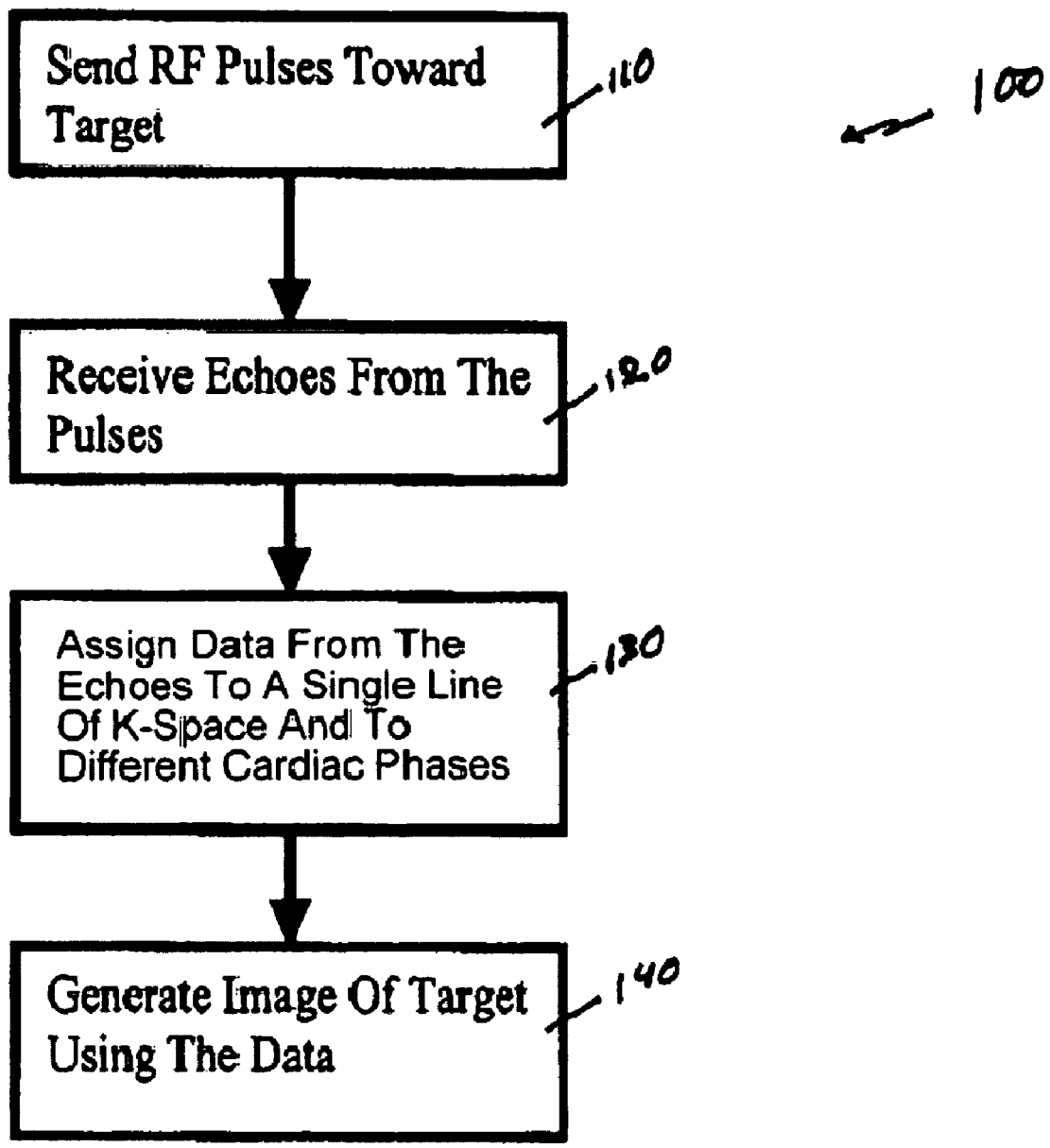
FIG. 1 is a flow diagram of one exemplary embodiment of a phase-train imaging ("PTI") method for generating magnetic resonance images according to the present invention.
Figure 2:
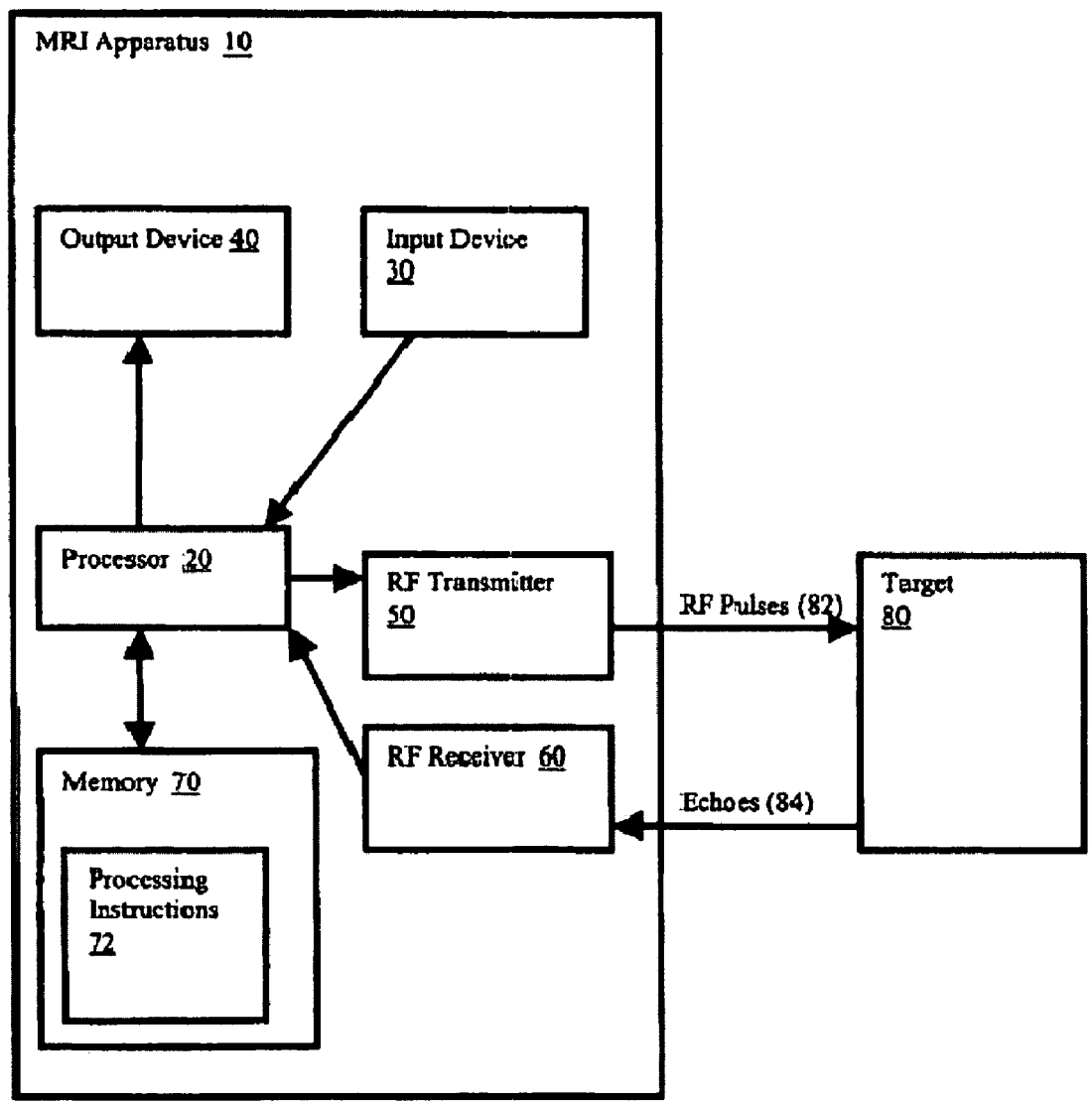
FIG. 2 is an exemplary embodiment of a magnetic resonance imaging ("MRI") apparatus according to the present invention which may be used to implement the method described with respect to the flow diagram of FIG. 1.

FIG. 1 shows a flow diagram of one exemplary embodiment of a phase-train imaging ("PTI") method 100 for generating magnetic resonance images according to the present invention. FIG. 2 shows an exemplary embodiment of an MRI apparatus 10 according to the present invention which may be used to implement the method 100 described below with respect to FIG. 1.

For example, as shown in FIGS. 1 and 2, a series of radio frequency ("RF") pulses 82 can be transmitted in step 110 by an RF transmitter 50 of the MRI apparatus 10 toward a target 80. In one exemplary embodiment, the exemplary method 100 can be applied to cardiac MRI techniques, and the target 80 may be patient's cardiac region. The series of RF pulses 80 can generate echoes 84 from the target 80, which may be received (in step 120) by an RF receiver 60 of the MRI apparatus 10. In one exemplary embodiment, a single device, e.g., a transceiver, can be used as both an RF receiver 60 and an RF transmitter 50. Because the multiple echoes 84 are acquired, the number of the RF pulses 82 used by the exemplary method 100 can be correspondingly smaller than those generally needed in conventional single-echo sequences. As a result, according to the exemplary embodiments of the present invention, any magnetization-preparation effects (e.g. tags) can persist for longer durations.

The received echoes 84 may be processed by the processor 20 of the MRI apparatus 10 using instructions 72 which, e.g., may be stored in memory 70. The processor 20 extracts data from the received echoes 84, and assigns the data in step 130 from the echoes 84 to a single line of k-space. The data may be stored by the MRI apparatus 10, for example, also in memory 70. In one exemplary embodiment of the present invention, the MRI apparatus 10 can be a cardiac MRI apparatus, and the target may be patient's cardiac region. In this exemplary embodiment, data from the each of the echoes 84 is assigned to the same k-space line, and to different cardiac phases. Because the echo data acquire the same k-space line for different cardiac phases, no "complex" phase discontinuity results from this approach. "Complex" phase-based ghosting artifacts generally do not exist because the same line in k-space is used for different cardiac phases.

After assigning the echo data to the single line of k-space, the processor 20 can generate an image of the target 80 in step 140 to be displayed, for example, on an output device 40. In one exemplary embodiment of the present invention, the processor 20 can further apply a parallel processing technique to the data, such as a time-adaptive sensitivity encoding ("TSENSE") or similar technique after assigning the data. Parallel processing used in connection with the phase-train imaging approach can allow for a creation of high resolution cardiac imaging in a single breath-hold duration. Because multiple echoes may be used, the number of RF pulses 82 that can be used is inversely proportional to the number of echoes 84 which were acquired. For example, in one exemplary embodiment according to the present invention, 3-5 echoes 84 may be used, implying 67-80% reduction in the number of RF pulses 82 which were required. By decreasing the number of pulses 84 utilized the magnetization preparation (i.e., tags) can remain longer.

The exemplary embodiment of the MRI apparatus 10 of FIG. 2 may also include an output device 40, such as a display, a printer for displaying, and/or printing the resulting image of the target 80. The exemplary MRI apparatus 10 of FIG. 2 can further include an input device 30, for example, for sending instructions to the processor 20 to cause processor 20 to transmit the RF pulses 82, so as to process the data received from the echoes 84, and display the resulting image of the target 80.

Figure 3:
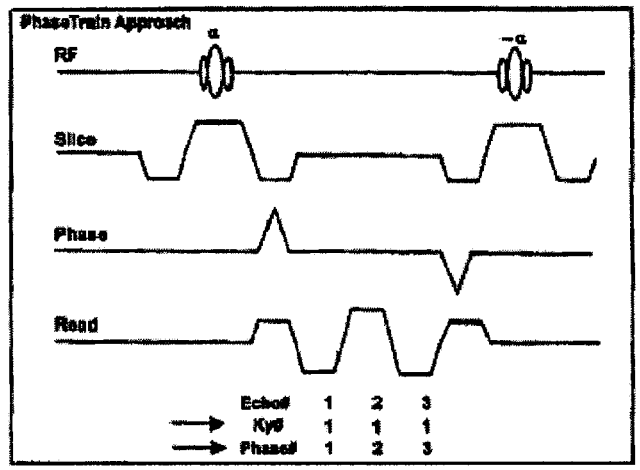
FIG. 3 is a graph of an exemplary application of the method of PTI according to an exemplary embodiment of the present invention based on a predefined repetition rate.
Figure 4:
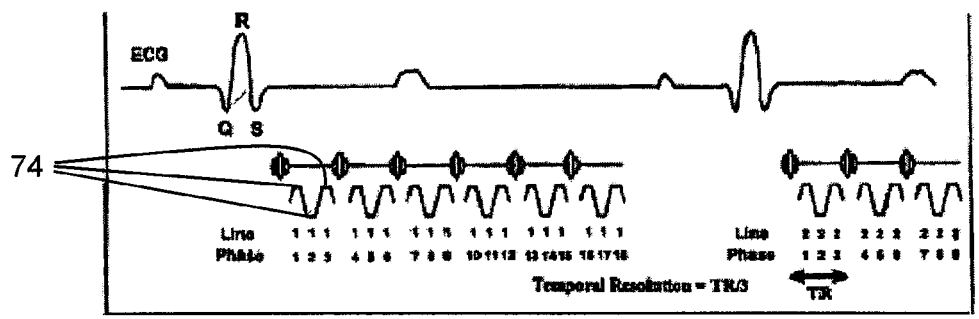
FIG. 4 is a graph of an exemplary application of the method of PTI according to an exemplary embodiment of the present invention based on a predefined parallel imaging rate.
Figure 5:
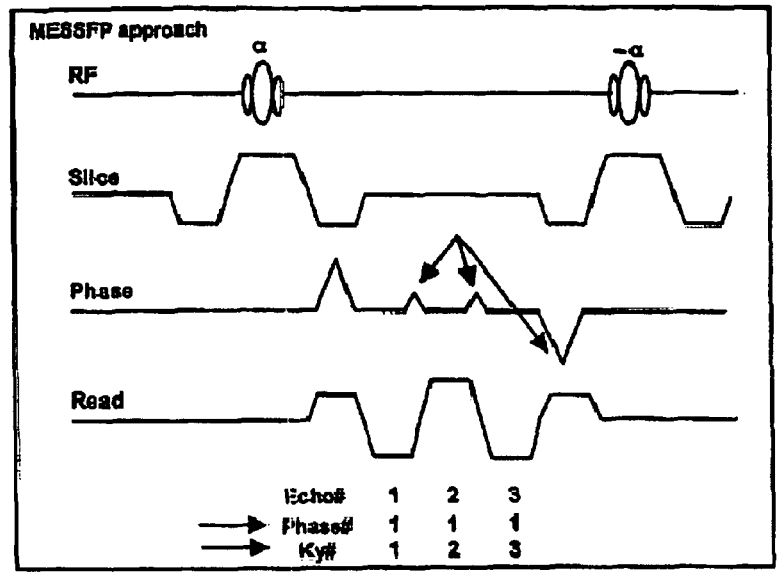
FIG. 5 is a graph of an exemplary application of a conventional MESSFP technique based on a predefined repetition.
Figure 6:
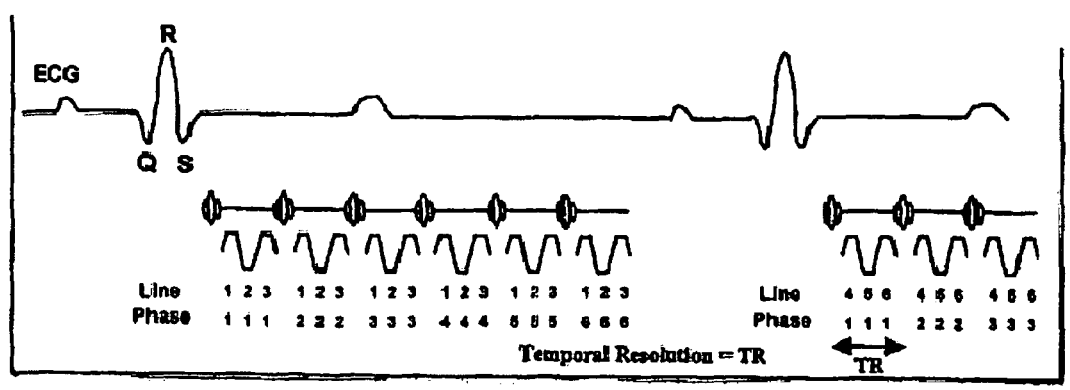
FIG. 6 is a graph of an exemplary application of a conventional MESSFP technique based on a predefined cardiac cycle and predefined parallel imaging rate.

FIG. 3 illustrates a graph of an exemplary application of and possible pulses generated by the exemplary method 100 of phase train imaging ("PTI") according to the present invention based on a predefined repetition rate. FIG. 4 illustrates a graph of an exemplary application of the method 100 of PTI according to the present invention based on a cardiac cycle which generates ECG readings and based on the pulses shown in FIG. 3. As shown in FIGS. 3 and 4, the phase train processing instructions 72 may assign data from each echo 74 to a separate cardiac phase, rather than acquiring multiple "complex" phase-encode lines. FIG. 5 illustrates a graph of and pulses generated by an exemplary application of a conventional a multiecho steady-state free precession ("MESSFP") technique based on a predefined repetition rate. FIG. 6 shows a graph of an exemplary application of the conventional MESSFP technique based on a predefined cardiac cycle. FIGS. 5 and 6 are provided to illustrate the differences in data processing with the exemplary embodiment of the method 100 of the present invention (the results of which are shown in FIGS. 3 and 4)

Second Exemplary Embodiments

The MESSFP approach called Phase Train Imaging (PTI) (e.g., see V. M. Pai et al. "Phase train approach for very high temporal resolution cardiac imaging," JCMR 2005; 7(1):98-99) can permit the acquisition of extremely high temporal resolution cine datasets in relatively short breath-hold durations. In this exemplary approach, unlike conventional MESSFP approaches, each set of echoes following an RF excitation pulse can acquire the same k-space line, and may be assigned to a different cardiac phase. Since all the echoes acquire the same k-space line for different cardiac phases, there may likely be no "complex" phase discontinuity in the "complex" phase-encode direction associated with this approach; since multiple echoes can be acquired, the number of RF pulses may be correspondingly smaller than that for single echo sequences, and effects of magnetization preparation pulses such as tagging can persist for a relatively longer duration. In addition, PTI is inherently more efficient, as may be defined by the ratio of sampling (e.g., readout) time to TR, than the conventional MESSFP sequences, as likely little or no time is wasted in blipping in the "complex" phase-encode direction. This approach may permit an acquisition of cine data with an average temporal resolution of 1.5 ms in breath-hold durations of 16 to 24 heartbeats.

In the exemplary PTI approach, while zero—the moments may be nulled for all echoes, the first moment nulling at the center of k-space is usually observed only on the odd echoes (see echoes 1 and 3 shown in FIG. 7(a)). Since each echo can acquire the same line of k-space, such non-nulling of a first moment for the even echoes can represent an additional "complex" phase, which may be equivalent to the application of a bipolar gradient. Such nonzero first moment of the gradients may likely produce "complex" phase shifts due to motion, which can be used to measure velocity along the gradient. By swapping the readout and "complex" phase-encode gradient axes, it is possible to use two successive scans to acquire in-plane flow data with this approach.

Exemplary Testing

The exemplary "complex" phase contrast PTI (PCPTI) sequence has been implemented on a Siemens Avanto scanner (Siemens Medical Solutions, Malvern, Pa.), and tested on healthy human volunteers. To test the capability of this sequence to estimate cardiac flow, a conventional, manufacturer-supplied, retrogated PC-FLASH cine sequence was also used to acquire in-plane flow data. Sequence parameters used in this test were: PCPTI: Echo train: 3, TR/TE: 6.7 ms/2.0 ms (to the first echo), inter-echo spacing: 0.82 ms, flip angle: 60°, field-of-view: 370×277.5 mm$^2$, Resolution: 256×48 pixels, SENSE rate: 2, breath-hold duration: 24 heartbeats, total cardiac phases acquired: 441, acquisition window/heartbeat: 900 ms. PCFLASH: TR/TE: 52/2.9 ms, flip angle: 30°, field-of-view: 320×240 mm$^2$, Resolution: 256×126 pixels, Segments: 7, breath-hold duration: 20 heartbeats, retrogated cardiac phases: 16, Venc: 250 mm/s in Head-Feet (HF) direction, 150 mm/s in Left-Right (LR) direction. For PCPTI, "complex" phase difference (cPD) data was calculated as cPD=$\theta_2$-$\theta_1$, where $\theta=\tan^{-1}(S_i/S_r)$, 1 and 2 refer to the first and second echoes in the echo train, and i and r represent the imaginary and real parts of the complex signal S. In the PCPTI approach, each echo train (i.e. train of echoes between RF pulses) provides one data point for the "complex" phase difference map; thus the temporal resolution for the PD study is 6.7 ms, and the number of cPD cardiac phases is: total cardiac phases acquired/echo train length (or 441/3=147 cardiac phases).

FIGS. 8(a)-(c) and 9(a)-(c) illustrate the exemplary results for flow encoding in the HF and LR directions, respectively. FIGS. 8(a) and 9(a) show representative PD images for the two encodings. Normalized signal intensity plots were generated for regions-of-interest (ROIs) placed in the left ventricle (LV) and pulmonary artery (PA). These plots are shown in FIGS. 8(b) and 8(c), and FIGS. 9(b) and 9(c), respectively, for the PCPTI (●) and PCFLASH (○) approaches as shown therein. Normalized plots are shown in these drawings only to mid-diastole.

The PCPTI approach can correlate well with the conventional PCFLASH sequence in tracking the velocity component in the HF direction for both the left ventricle and the pulmonary artery. Due to the generally lower velocity in the LR direction, both sequences provide relatively noisy data for the LR encoding. Even though this is the case, the two sequences may reasonably agree in the systolic portion of the cardiac cycle. Both sequences can provide unreliable LR velocity estimates in the diastolic cardiac phase. The PCPTI sequence likely provides the highest temporal resolution to-date for looking at in-plane flow patterns, with each velocity component being acquirable in a single breath-hold. For example, as shown in FIG. 10(b), the high temporal resolution enables the capture of the end-systolic back-flow in the HF direction, which can be missed by the lower resolution PCFLASH sequence.

Third Exemplary Embodiments

Exemplary Approach to Encode in all 3 Directions

For example, an echo train of 3 echoes can enable a first moment nulling in the Readout direction (beside the inherent zero-th moment nulling) at the end of each TR (repetition time), thus maintaining the conditions for trueFISP imaging (e.g., zero-th and first moments are generally nulled in the Slice Select and "complex" phase-encode directions in this approach). However, the 3-echo implementation of PCPTI can be primarily provided to encode the flow in-plane. In addition, because the implementation may have a long TR, it can potentially give rise to off-resonance banding artifacts if encoding for smaller velocities is attempted. An alternate approach can be to use a 2-echo implementation. One exemplary approach to achieving first moment nulling at the end of each TR with a 2-echo sequence can be to either implement a bipolar gradient following the second readout gradient, or to use a flyback gradient between the two readout gradients. Both techniques may utilize almost equal time for achieving first moment nulling (e.g., see D. A. Herzka et al. "Multishot EPI-SSFP in the heart," Magn Reson Med 2002; 47(4):655-64), and yield a shorter TR than a 3-echo readout scheme. This exemplary approach can provide an alternative to the 3-echo encoding scheme for achieving flow encoding in all 3 directions and permitting a wider range of encoding velocities.

a. Encoding In-Plane.

Figure 10A:
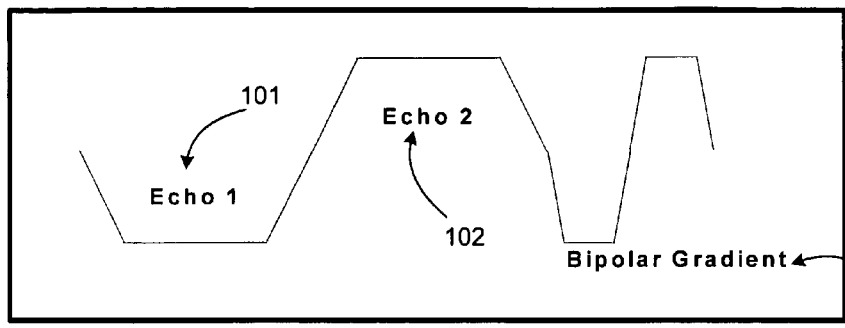
FIG. 10(a) is an exemplary application of possible 2-echo implementation, with the encoding in provided in a readout direction.
Figure 10B:
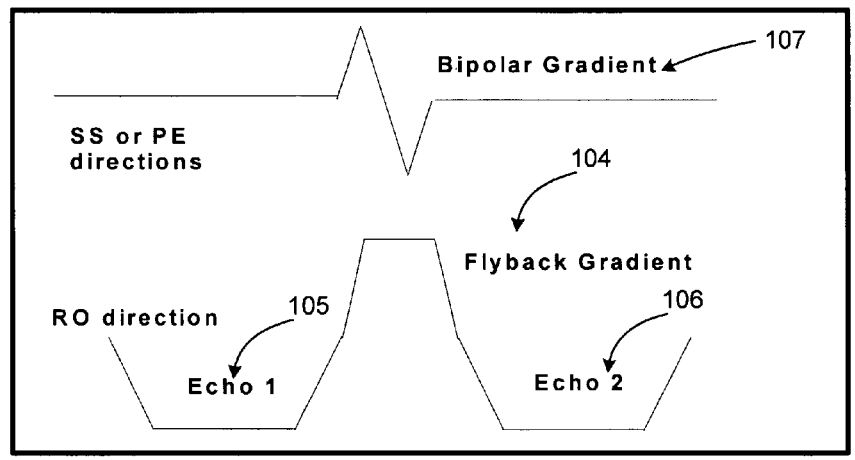
FIG. 10(b) is the exemplary application associated with FIG. 10(a), with the encoding in provided in PE or SS directions.

FIG. 10(a) illustrates an exemplary implementation of the 2-echo scheme to encode for flow in the in-plane direction. While the graph of FIG. 10(a) shows the readout ("RO") direction, the concept can be applied to the PE direction very easily by swapping the RO and PE direction gradients. In this exemplary approach, the bipolar gradient 103 to null the first moment can be applied after the second echo readout 102. Thus while the first moment can be nulled at the end of the TR, it is generally not nulled between the first echo 101 and second echo 102, permitting encoding for velocity. The first moment can be varied deliberately by changing the gradient strength, receiver bandwidth and/or the duration of the readout gradients. In this manner, it is possible to provide a wider range of velocities that can be encoded for, and the first moment can be nulled by varying the size and/or the duration of the bipolar gradient 103 applied subsequent to the readout.

b. Encoding Through-Plane

FIG. 10(b) illustrates an exemplary implementation of the 2-echo scheme to encode for flow in the through-plane direction in accordance with the present invention. This exemplary approach can also be used to encode for the flow in the "complex" phase-encoding direction (or any direction, e.g., perpendicular to the readout direction). In this exemplary approach, instead of using the bipolar gradient subsequent to the second readout, a flyback gradient 104 can be implemented between the first echo 105 and the second echo 106 to null the first moment on, e.g., both echoes. At the same time, a bipolar flow-encoding gradient 107 can be applied in the direction perpendicular to the readout direction, permitting encoding for flow in that direction (e.g., a through-plane, and can also be the "complex" phase-encoding direction).

c. Yet Another Exemplary Embodiment

Figure 10C:
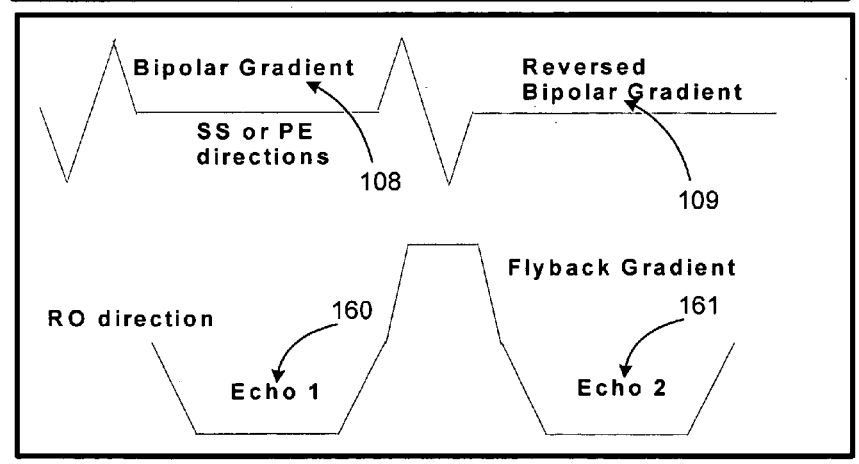
FIG. 10(c) is the exemplary application associated with FIG. 10(a), with the encoding in provided in a PE direction.

FIG. 10(c) shows another exemplary embodiments of the concept/approach described herein above, e.g., and application of a bipolar gradient 108 before the readout scheme is started, and then a further application of an inverted bipolar gradient set 109 (e.g., with reversed signs), such that while the first echo 160 encodes motion in one direction (e.g., in the same plane), the second echo 161 will encode for motion in the opposite direction. This will permit cancellation of non-motion related "complex" phase shifts, and eliminate the need to acquire an additional reference scan.

In accordance with exemplary embodiments of the present invention, the echo trains may be of any length. For example, echo trains with an odd number of echoes may be particularly useful for measuring flow acceleration or higher-order time derivatives of motion. If the echo-train is set-up in such a manner as to null the zero-th and first gradient moments after the $3^{rd}$ echo (considering a 3-echo echotrain as an example) while non-nulling the second gradient moment, then such technique can be used to measure the acceleration. Other higher-order derivatives can be similarly implemented and acquired.

Fourth Exemplary Embodiments a. Multiple Directions Encoding Within a Breath-Hold Scan.

While the conventional implementation of PCPTI can permit very high temporal resolution flow imaging in one direction (for example—the x direction), another exemplary embodiment of PCPTI in accordance with the present invention can enable the acquisition of flow information in multiple directions (e.g., at a relatively lower temporal resolution). In this exemplary case, instead of RR-x-x-x-x-x-x-RR type of acquisition (where RR may be the start of the new cardiac cycle), it is possible to use either RR-x-y-x-y-x-y-RR (an example of 2D flow quantification) or RR-x-y-z-x-y-z-RR (an example of 3D flow quantification).

b. Increased Spatial Resolution by Encoding Multiple Lines Per Cardiac Cycle

PCPTI can yield very high temporal resolution flow imaging data. However, when used for breath-holding clinical studies, this exemplary approach may provide a spatial resolution in one direction (e.g., the "complex" phase-encoding direction) due to the preference to minimize the duration that the patient holds her/his breath. Since quantitative "complex" phase contrast imaging can suffer at lower spatial resolution, an exemplary embodiment of the PCPTI technique in accordance with the present invention can be employed which may sacrifice some of the high temporal resolution to recover some spatial resolution in the "complex" phase-encoding direction. If, e.g., the acquisition in the x direction is RR-1-2-3-4-5-6-RR, where RR is the start of the cardiac cycle, and the numbers may indicate the cardiac phase number. This can be the standard implementation of the PCPTI sequences, with one "complex" phase-encoding line being acquired for each cardiac cycle (when no parallel imaging implementation is considered). Yet another exemplary embodiment may be RR-1-1-2-2-3-3-RR, wherein two "complex" phase-encoding lines are acquired for each cardiac cycle over each cardiac cycle (again, this assumes no parallel imaging implementation is used). Thus, for the same breath-hold duration, it is possible to double the number of "complex" phase-encoding lines acquired, while reducing by half the temporal resolution achieved. Accordingly, the prior implementation(e.g., acquired 24 "complex" phase-encoding lines with a temporal resolution of 6 ms, this implementation) would acquire 48 "complex" phase-encoding lines with a temporal resolution of 12 ms, over the same scan duration.

c. Combination of (a) and (b) Permitting Data Acquisition at the Same Time Stamp While procedure (a) allows for an acquisition of volumetric flow information in a breath-hold duration, it may introduce a temporal delay between the data acquired in the 3 directions used. For a number of situations, this delay may not be very significant, and can be acceptable. However, there may be cases where it is important to acquire the volumetric flow data with the same temporal time stamp; for these cases, an alternate procedure may be desired. This exemplary alternate procedure can be a combination of the two approaches described above which can be used to achieve this goal. In this exemplary case, the procedure indicated in step (b) can be primarily used to enable volume imaging rather than to improve spatial resolution, if the examinations may be performed over the same scan duration.

Example

Approach proposed in procedure (a): RR-x-y-z-x-y-z-RR-x-y-z-x-y-z-. . . .

Approach proposed in procedure (b): RR-x1-x1-x2-x2-x3-x3-RR-x1-x1-x2-x2-x3-x3-RR.

Proposed approach in procedure (c):

Interleaved: RR-x1-x1-x2-x2-x3-x3-RR-y1-y1-y2-y2-y3-y3-RR-z1-z1-z2-z2-z3-z3-RR . . . .

Total: RR-x1-x1-x2-x2-x3-x3-RR-(Complete x scan)-RR-y1-y1-y2-y2-y3-y3-RR-(Complete y scan)-RR-z1-z1-z2-z2-z3-z3-RR.

This exemplary procedure may have the added advantage that it does not interrupt steady-state (unlike procedure (a)), and thus can permit a performance of the SSFP imaging in the 3 directions. However, for situations where this approach may be used in breath-holding conditions, the spatial resolution in the "complex" phase-encoding direction may become an issue with this exemplary procedure.

Fifth Exemplary Embodiments

Another exemplary implementation of PCPTI in accordance with the present invention is to acquire data in a segmented manner. By this exemplary implementation, it is possible to trade the high temporal resolution provided in the basic PCPTI technique, to improve the spatial resolution achievable over the same duration of the scan. The conventional gated/triggered implementation of the PCPTI procedure can generally acquire one line of k-space for a given cardiac phase (or time stamp) per trigger signal. In an exemplary segmented implementation in accordance with the present invention, multiples lines of k-space are acquired for a given cardiac phase (or time stamp) per trigger signal. By this logic, the number of cardiac phases can be acquired in a triggered interval (e.g., the time between two successive trigger signals) by a segmented approach may be less than (or equal to, if the number of segments is one) the number of cardiac phases acquired by an non-segmented approach. On the other hand, for a given total scan duration, the number of k-space lines that can be acquired by a segmented approach will likely be more than (or equal to, if the number of segments is one) a non-segmented approach.

Example

Non-segmented: if 30 lines of k-space data are acquired over 30 seconds (trigger signals separated by 1 sec) for 20 cardiac phases (or 20 time points over the 1 second) by the non-segmented method, then each cardiac phase gets one line of k-space acquired in 1 second.

On the other hand, if a segmented implementation with two segments is considered, then over a period of 30 seconds, 60 lines of k-space data can be acquired for 10 cardiac phases (or 10 time points over the 1 second). In this exemplary case, each cardiac phase can receive two lines of k-space acquired in 1 second.

One of the main advantages of the segmented approach in this scenario is the increase in the spatial resolution in the "complex" phase-encoding direction (e.g., the number of lines of k-space acquired). The higher the number of lines of k-space acquired, the higher the spatial resolution which may be achieved. For applications where the flow signal variation does not require the high temporal resolution, but requires higher spatial resolution due to the small size of the vessels (such as blood vessels in the renal and hepatic systems), this exemplary approach can permit a higher accuracy in quantifying the flow due to the higher spatial resolution in the "complex" phase-encoding direction. The spatial resolution in the frequency-encoding direction is independent of this scheme, and high spatial resolution in the frequency-encoding direction can be attained in both segmented and non-segmented approaches trivially.

Sixth Exemplary Embodiments

This exemplary technique in accordance with the present invention can combine the multi-echo gradient recalled EPI approach, parallel imaging, and a unique approach to acquiring individual images for each of the echoes of the segmented acquisition. Since the temporal resolution of snapshot imaging can be determined by the time taken to reach the center of frequency space (or k-space, as it is conventionally referred to), the proposed approach can acquire the data in such a way that each echo (in the multi-echo train) reaches the center of k-space at a different time point. By uniformly distributing the time utilized for each echo to reach the center of k-space, it is possible to effectively obtain a true temporal resolution to be the total acquisition time divided by the number of echoes in each echo train. For example, if 120 lines of data to be acquired are considered with a 3-echo echo train (without considering parallel imaging), then the first echo could acquire the center of k-space at the $0^{th}$ instance, the second echo would be at the $40^{th}$ instance and the third echo would acquire the center of k-space at the $80^{th}$ instance (this would be the 0-40-80 case). This exemplary implementation may also permit staggered temporal resolution to be achieved, for example, it is possible to establish the study such that the first echo acquires the center of k-space at the $30^{th}$ instance, the second at the $60^{th}$ instance and the third at the $90^{th}$ instance (this would be the 30-60-90 case).

If multiple repetitions are considered, then another exemplary implementation for the 0-40-80 case can be achieved by acquiring a short 40 line scan upfront. The previous example illustrated above may make it difficult to determine the time resolution of the $0^{th}$ instance (since it is likely the same as the $120^{th}$ instance). If, however, 40 lines are acquired before the start of the first acquisition, then a true 0-40-80 temporal breakdown can be achieved. When combined with multiple repetitions, the last 40 lines of the previous repetition then serve as the first 40 lines for the first echo in the current repetition.

The size of the echo train thus governs the highest temporal resolution that can be achieved for a given parallel imaging factor (e.g., parallel rates of 1 to 4 in two dimensions). This, in turn, can be controlled by the T2* of the specimen being studied.

Ghosting is an artifact that is generally associated with multi-echo acquisitions. However, since each echo can be assigned to a totally separate image, unlike conventional multi-echo implementations, this problem can be significantly minimized. If one uses a SSFP approach, zero-th and first moment nulling can be achieved relatively easily in the slice-encoding and frequency-encoding directions; while zero-th moment nulling can be achieved in the "complex" phase-encoding direction, it may be non-trivial (or impractical) to achieve first moment nulling in the "complex" phase-encoding direction, due to the large blips present.

Figure 11:
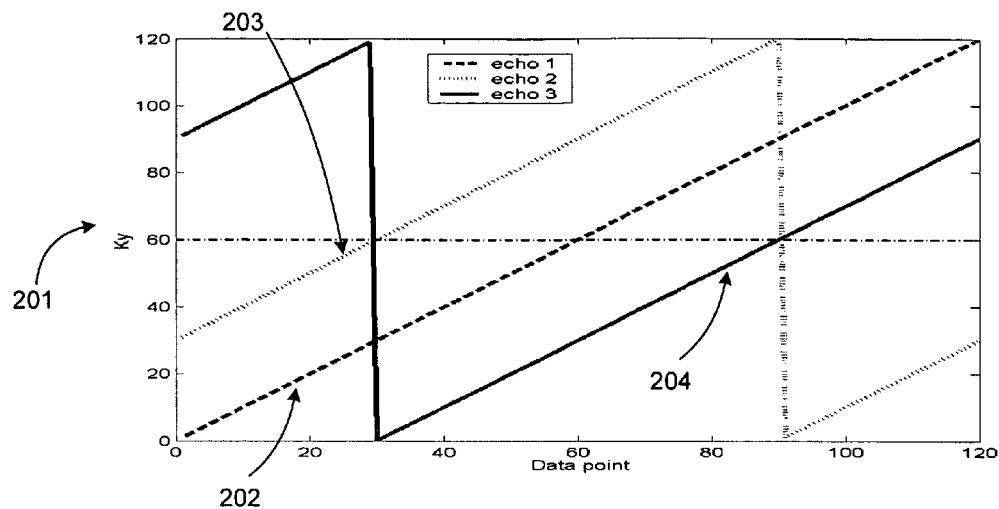
FIG. 11 is an exemplary graph of k-space travel by each echo of a multi-echo sequence in accordance with an exemplary embodiment of the present invention.
Figure 12:
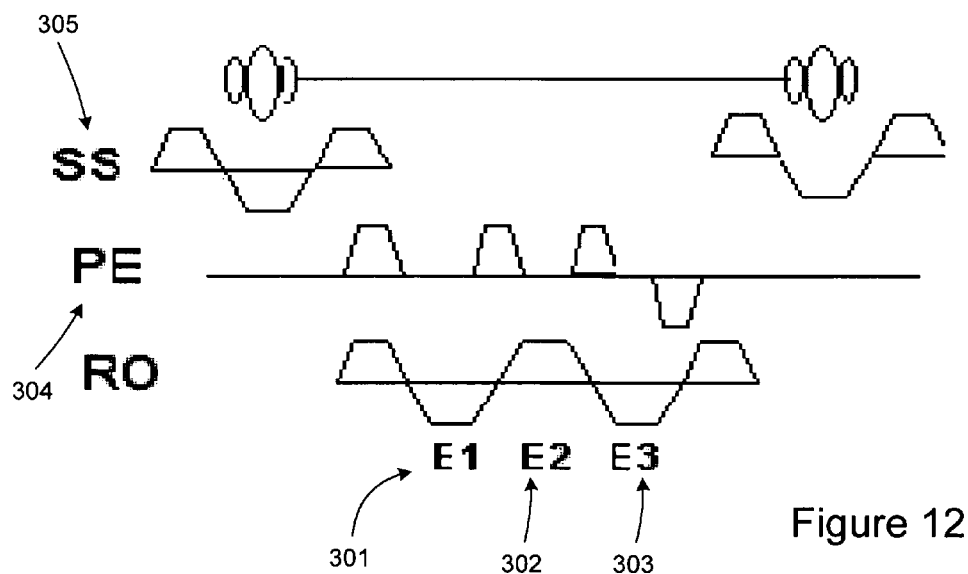
FIG. 12 is an exemplary application of the exemplary pulse sequences per TR.

The exemplary embodiments of the present invention may use a multi-echo SSFP sequence in combination with parallel imaging. The exemplary embodiments of the present invention may also be utilized without parallel imaging. For example, in order to have high temporal resolution, each echo generally encodes a separate image, such that the center of k-space for each echo is traversed at a different instance in time. FIG. 11 shows a graph of a travel in ky direction 201 by each echo (including depicted echo 1—202, echo—2 203, and echo 3—204). FIG. 12 shows a graph of 3 echoes comprising echo 1—301, echo 2—302, and echo 3—303, along with the large "blips" used in the "complex" phase encoding direction. For the exemplary sequence described herein with reference to FIG. 12, the zero-th and first moments can be nulled in the slice select and readout direction 304, while only the zero-th moment may be nulled in the "complex" phase encoding direction 305. While it may be possible to null the first moment in the "complex" phase-encoding direction, the large time duration for achieving such nulling makes such option would likely be non-feasible In this exemplary reordering scheme, echo (and image) 1—202, 301 can encode the center of k-space at 50 ms, echo 0 at 100 ms, and echo 2—203, 302 at 150 ms from the start of the acquisition.

Seventh Exemplary Embodiments

This exemplary technique in accordance with an exemplary embodiment of the present invention may be used for proton imaging, including without limitation T1 mapping. This may be accomplished by combining inversion pulses (and similar magnetization preparation schemes) with the multi-echo imaging to obtain the images with desired contrast or needed contrast. This exemplary technique may be used with T1 mapping. In such case, an inversion pulse may applied before a multi-echo readout scheme is implemented.

This exemplary technique can be used with cardiac applications or non-cardiac applications. Cardiac applications may include those which are dependent on cardiac cycle. Non-cardiac applications can include those which are not dependent on the cardiac cycle.

For non-cardiac application, the exemplary embodiment of the present invention can be useful for obtaining data on organs where cardiac gating may not be an affecting factor. In such case, the inversion pulse can be played out after either a triggering pulse is available or in a non-triggered mode. Subsequently, the multi-echo technique can be used to acquire a large number of images such that each image is acquired at a different inversion time (i.e. time from the inversion pulse). If a multi-echo module (MEM) can be defined as the number of lines of k-space acquired to generate one image from each echo, then a user-defined number (n) of modules can be acquired subsequent to the inversion pulse; with the total duration of the n modules being independent of the cardiac duration. Thus, for example, if the heart rate is 1 heartbeat per second, this implementation can acquire MEMs for 46 seconds before the next inversion pulse is applied. The exemplary non-cardiac application is depicted in an exemplary table of FIG. 15.

For a cardiac application, there may be a difference from non-cardiac application in that the sequence may be EKG gated. This scenario may reduce the number of MEMs that can be acquired subsequent to the EKG pulse, and may minimize the number of inversion times that may be achieved in a given cardiac interval. To increase the temporal resolution of the inversion times imaged, the reordering scheme used for the MEM can be varied per cardiac interval; thus for example if MEM1 is a 3-echo module which has the zero-crossings at 10, 50 and $90^{th}$ instance of a 120 lines acquisition, then an acquisition scheme such as that shown in an exemplary table of FIG. 16 can be used to increase the number of inversion times imaged. In this exemplary implementation, MEM2 can have zero crossings at 20, 60, 100; MEM3 can have zero crossings at 30, 70, 110, and MEM4 can have zero crossings at 40, 80 and 120. A similar multiMEM approach can be used for the non-cardiac implementation, as shown in an exemplary table of FIG. 17. In this exemplary figure, n represents the number of heartbeats used to acquire the images corresponding to the requisite number of inversion times.

An alternate exemplary implementation can use the same MEM approach/technique as described herein above, with a change of the time delay between the inversion pulse and the start of the MEM. Such exemplary approach can be used in both cardiac and non-cardiac implementations. A combination of a multiMEM approach and the time delay between the inversion pulse and the MEM (e.g., thus minimizing the range of MEM variability required) may be employed in accordance with another exemplary embodiment of the present invention.

Eighth Exemplary Embodiments

Figure 18:
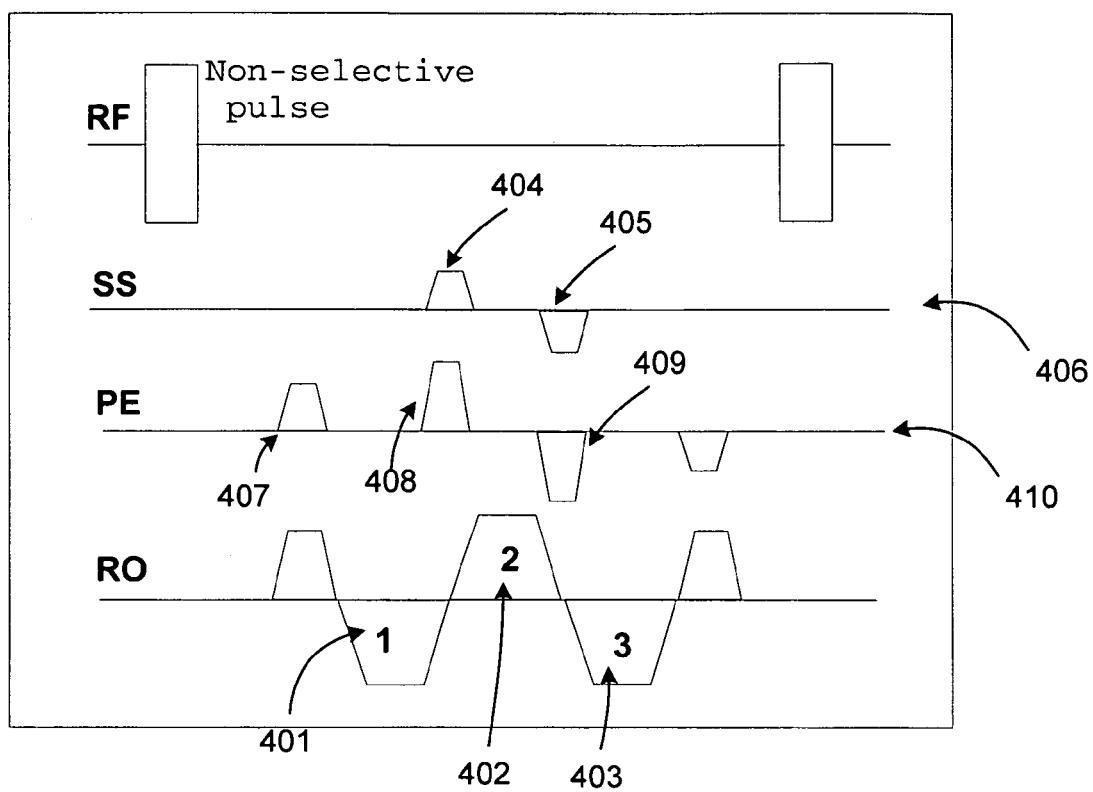
FIG. 18 is a graph providing results of an exemplary application of the exemplary pulse sequences for multislice imaging of a sample using the multiMEM technique.

This exemplary technique in accordance with yet another exemplary embodiment of the present invention can be used for perfusion imaging (e.g., conventionally performed previously by using a saturation pulse rather than an inversion pulse) on a single slice. For multislice perfusion imaging, a multislice MEM implementation may be utilized. In this exemplary technique in accordance with the exemplary embodiments of the present invention, each echo can be used to acquire a different slice of the imaged organ. When combined with a multiMEM approach/technique, each slice may be acquired at a different time point in the imaging cycle, as shown in FIG. 18. For example, FIG. 18 shows an exemplary graph of 3 echoes comprising echo 1—401, echo 2—402 and echo 3—403. Different locations in space can be achieved by blips 404 and 405 in the SS direction 406. The echoes 2—402 and 3—403 for slices corresponding to the blips 404 and 405 can be different from the echo 1—401 which is obtained for a center slice of the 3-slice set (i.e. it has no blip in the SS direction 406). The center of k-space for each of these locations is reached at different time points due to the blips 407, 408 and 409 in the "complex" phase-encode direction (PE) (410) Thus, the example indicated above (i.e., zero crossings at 30, 60 and 90 in an acquisition of 120 lines) is considered, then the slice 1 can be acquired first (first echo 1—401), the slice 2 is acquired by echo 2—402, a duration 30 points later than slice 1 and slice 3 can be acquired by echo 3—403 after a duration 30 points later than slice 2. Reordering schemes can be employed so as to arbitrarily vary the time between the acquisition of the individual slices. The reordering scheme may be arbitrary. The number of slices that can be acquired in this exemplary manner may be about equal to the number of echoes in a multiMEM. T2* effects may also affect the number of echoes that can comprise a MEM. When bSSFP is employed, the number of echoes may be limited to 5 or less.

This exemplary technique in accordance with the exemplary embodiments of the present invention may employ a balanced SSFP readout scheme and/or various other readout schemes such as spoiled SSFP readouts (e.g., GRASS, FLASH, etc).

While the example illustrated in FIG. 18 uses a non-selective RF volume excitation, of course different approaches to achieve this excitation can be implemented, including slab-selective excitation, multi-RF pulse excitation, spectrally-selective pulse excitation, etc to excite the various locations in space.

Exemplary Tests

Tests have been performed using SENSE rate of 4 on a clinical whole-body 1.5 T Siemens Avanto scanner using a 3×4×2 element coil constructed in-house. $^3$He gas was polarized by a spin exchange with an optically pumped rubidium vapor using a GE Healthcare helium polarizer. Helium polarized at 35-50% was diluted with $N_2$ to provide a net polarization of 12%, and transferred to 1 liter Tedlar plastic bags and delivered to a healthy subject. Imaging was initiated during slow exhalation of the helium and the volunteer was permitted to breathe freely during the scan. The imaging matrix was 128×128 on a FOV of 340×340, yielding a spatial resolution of 2.65 mm×2.65 mm, and a flip angle of 15 degrees was used for the RF pulses.

Figure 13:
FIG. 13 is an exemplary set of images acquired for each echo in accordance with an exemplary embodiment of the present invention.
Figure 14:
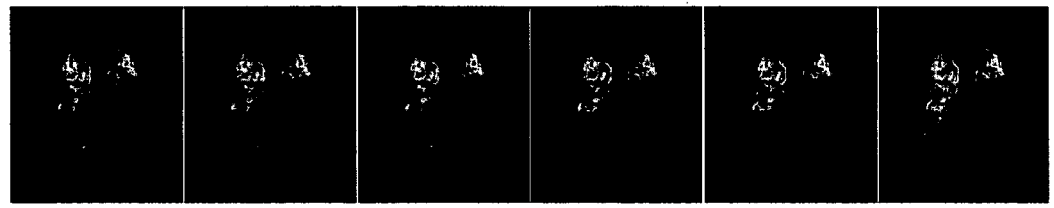
FIG. 14 is an exemplary set of images of a first six frames of the exemplary acquisition in accordance with one exemplary embodiment of the present invention.

FIG. 13 shows the images acquired by each of the three echoes in the echo train. As shown, there is a minimal interference between the echoes, since the data are individually reconstructed. FIG. 14 shows the images from the first 6 frames (3 echoes×2) of a free-breathing scan of a normal volunteer inhaling hyperpolarized helium. Since SENSE rate 4 was used, each 3-echo set takes 170 ms to acquire, thus yielding a temporal resolution of 57 ms.

Utilizing a combination of the exemplary multi-echo SSFP sequence, a unique reordering scheme increased temporal resolution or a combination of increased temporal and spatial resolution may be achieved. The invention may optionally employ parallel reconstruction algorithms to further achieve increase temporal resolution and speed. True temporal resolution of 50-60 ms has been achieved for a spatial resolution of 2.35 mm×2.35 mm. This exemplary technique in accordance with the present invention may have certain advantages when compared with spiral imaging or other imaging methods. These advantages may include increased simplicity and ease of implementation.

During reconstruction of a multi-echo readout of the form indicated in this exemplary application, it is possible that when the images reconstructed by individual echoes are combined together, a "flickering" or signal oscillation effect may be noticed. This usually can arise due to a chemical shift between the various species (e.g., fat and water), and because they generally do not refocus at the same time for all the echoes in a multiecho readout. One exemplary approach to minimizing this effect is to band pass filter the results in the time domain on the reconstructed images. This can be performed by a Fourier transformation along the time axis of the reconstructed images, applying a either a band-pass filter to accept the DC component (or a band-reject filter to reject the oscillatory components), and further applying an inverse Fourier Transformation to recover the reconstructed images with the "flickering" or oscillating effect likely minimized.

Although the present invention has been described with respect to particular embodiments thereof, variations are possible. The present invention may be embodied in specific forms without departing from the essential spirit or attributes thereof. In addition, although aspects of an implementation consistent with the present invention are described as being stored in memory, one skilled in the art will appreciate that these aspects can also be stored on or read from other types of computer program products or computer-readable media, such as secondary storage devices, including hard disks, floppy disks, or CD-ROM; a carrier wave from the Internet or other network; or other forms of RAM or read-only memory ("ROM"). It is desired that the embodiments described herein be considered in all respects illustrative and not restrictive and that reference be made to the appended claims and their equivalents for determining the scope of the invention. All publications referenced or listed herein are incorporated herein by reference in their entireties.

What is claimed is:

1. A method for obtaining information associated with a target, comprising:
forwarding a plurality of radio-frequency pulses toward the target;
receiving a plurality of echoes associated with each of the radio-frequency pulses, each particular one of the echoes being assigned to a different one of a plurality of particular images;
assigning data associated with each particular one of the echoes to at least one of
a). a single line of k-space and multiple phases associated with the target or time stamps thereof or
b). a plurality of lines of k-space for at least one particular phase of multiple phases associated with the target or at least time stamp; and
generating, as a function of the data, the particular images which include a first image and a second image of at least one portion of the target using a computing arrangement.

2. The method of claim 1, wherein at least one of the first image or the second image is generated using the data after the data has been assigned to the single line of k-space and to at least one of multiple phases of the target or time stamps thereof.

3. The method of claim 1, wherein the target is a cardiovascular region of a patient's body and the multiple phases include cardiac phases, and wherein the data is assigned from each of the separate echoes to at least one of separate corresponding cardiac phases or time stamps.

4. The method of claim 1, further comprising processing the data using a parallel processing technique after the data is assigned.

5. The method of claim 1, further comprising processing the data using at least one: a) a sensitivity encoding technique, b) a "complex" phased-array ghost elimination technique, c) a spatial harmonics technique, d) a generalized reconstruction using partially parallel acquisition technique, or e) a time-adaptive sensitivity encoding technique, after the data is assigned.

6. The method of claim 1, further comprising generating, as a function of the data, at least one of velocity data associated with the target or acceleration data associated with the target.

7. The method of claim 6, wherein at least one of the velocity data or the acceleration are provided in a form of at least of one a plot, a map, a graph, or a chart.

8. The method of claim 6, where at least one of the velocity data or the acceleration data are related to a flow of at least one fluid or a gas in an anatomical structure.

9. The method of claim 8, wherein at least one fluid is blood.

10. The method of claim 8, where at least one gas is a polarized gas or a hyperpolarized gas.

11. The method of claim 10, wherein the hyperpolarized gas is 3He.

12. A magnetic resonance imaging system, comprising:
a processor;
a radio frequency ("RF") transmitter provided in communication with the processor, wherein the transmitter is configured to forward at least one RF pulse to a target in response to a receipt of a signal from the processor; and
a RF receiver provided in communication with the processor, wherein the RF receiver is configured to receive data from the target based on a plurality of echoes generated by each particular one of the at least one RF pulse, and configured to forward the data to the processor, wherein the processor is configured to assign data from the echoes to a single line in k-space and to multiple phases associated with the target or time stamps thereof, wherein each particular one of the echoes is assigned to a different one of a plurality of particular images, and wherein the processor is further configured to generate the particular images which include a first image and a second image of at least one portion of the target as a function of the data.

13. The system of claim 12, wherein the RF transmitter is configured to generate RF pulses and forward the RF pulses toward a cardiac region of a patient in response to the signal received from the processor, and wherein the processor is configured to assign data from the echoes to the single line in k-space and to the multiple phases or the time stamps thereof, and configured to assign data from different echoes to different phases or different time stamps.

14. The apparatus of claim 12, wherein the processor is configured to generate at least one of velocity data associated with the target or acceleration data associated with the target as a function of the data.

15. The apparatus of claim 14, where at least one of the velocity data or the acceleration data are related to a flow of at least one fluid or a gas in an anatomical structure.

16. The apparatus of claim 12, further comprising processing the data using at least one: (a) a sensitivity encoding technique, (b) a "complex" phased-array ghost elimination technique, (c) a spatial harmonics technique, (d) a generalized reconstruction using partially parallel acquisition technique, or (e) a time-adaptive sensitivity encoding technique, after the data is assigned.

17. A magnetic resonance imaging system, comprising:
a first arrangement configured to forward at least one radio-frequency pulse toward a target;
a second arrangement configured to receive a plurality of echoes corresponding to each particular one of the at least one radio-frequency pulse;
a third arrangement configured to assign data received from each particular one of the echoes to at least one of (i) a single line of k-space and to multiple phases associated with the target or time stamps thereof, or (ii) a plurality of lines of k-space for at least one of a particular one of the phases or at least one time stamp, wherein each particular one of echoes is assigned to a different one of a plurality of particular images; and
a fourth arrangement configured to generate, as a function of the data, the plurality images which include a first image and a second image of at least one portion of the target.

18. The method of claim 17, wherein the echoes are assigned to a same location in space and time.

19. The method of claim 17, wherein the echoes are assigned to different locations in space and time.

20. The method of claim 17, further comprising obtaining the information for T1 mapping based on the plurality of images.

21. The method of claim 17, further comprising obtaining the information used for perfusion studies based on the plurality of images.

22. The method of claim 17, further comprising obtaining the information for a parallel image reconstruction based on the plurality of images.

23. The magnetic resonance imaging system of claim 17, wherein the fourth arrangement is configured to generate, as a function of the data, at least one of velocity data associated with the target, or acceleration data associated with the target.

24. The magnetic resonance imaging system of claim 23, wherein at least one of the velocity data or the acceleration data are related to a flow of at least one fluid or a gas in an anatomical structure.

25. The magnetic resonance imaging system of claim 17, wherein the target is a cardiovascular region of a patient's body and the multiple phases include multiple cardiac phases, and wherein the fourth arrangement is further configured to generate at least one of the first image or the second image using the data after the data has been assigned to the single line of k-space and to at least one of multiple cardiac phases or time stamps thereof.

26. The magnetic resonance imaging system of claim 17, wherein the fourth arrangement is further configured to process the data using at least one: (a) a sensitivity encoding technique, (b) a "complex" phased-array ghost elimination technique, (c) a spatial harmonics technique, (d) a generalized reconstruction using partially parallel acquisition technique, or (e) a time-adaptive sensitivity encoding technique, after the data is assigned.

27. A non-transitory computer-readable medium having stored thereon computer-executable software for performing a method of obtaining information associated with a target, the software comprising:
a first set of instructions capable of configuring a processor to cause a transmission of at least one radio-frequency ("RF") pulse toward the target;
a second set of instructions capable of configuring the processor to assign data from each of a plurality of echoes received from the target and associated with the at least one RF pulse to at least one of (i) a single line of k-space and to multiple phases associated with the target or time stamps thereof, or (ii) a plurality of lines of k-space for at least one of a particular one of the phases or at least one time stamp, wherein each particular one of echoes is assigned to a different one of a plurality of particular images; and
a third set of instructions capable of configuring the processor to generate, as a function of the data, the particular images which include a first image and a second image of at least one portion of the target.

28. The computer-readable medium of claim 27, wherein the third set of instructions are capable of configuring the processor to generate, as a function of the data, at least one of velocity data associated with the target or acceleration data associated with the target.

29. The computer-readable medium of claim 28, wherein at least one of the velocity data or the acceleration data are related to a flow of at least one fluid or a gas in an anatomical structure.

30. The computer-readable medium of claim 27, wherein the target is a cardiovascular region of a patient's body and the multiple phases include multiple cardiac phases, and wherein the third set of instructions are capable of configuring the processor to generate at least one of the first image or the second image using the data after the data has been assigned to the single line of k-space and to at least one of multiple cardiac phases or time stamps thereof.

31. The computer-readable medium of claim 27, wherein the third set of instructions are capable of configuring the processor to process the data using at least one: (a) a sensitivity encoding technique, (b) a "complex" phased-array ghost elimination technique, (c) a spatial harmonics technique, (d) a generalized reconstruction using partially parallel acquisition technique, or (e) a time-adaptive sensitivity encoding technique, after the data is assigned.

32. A method for obtaining information associated with a target, comprising:
forwarding a plurality of radio-frequency ("RF") pulses toward the target;
receiving a plurality of echoes associated with each of the pulses, wherein at least one of the echoes reaches a center of k-space at a first point in time and at least further one of the echoes reaches the center of the k-space at a second point in time which is different than the first point; and
generating a plurality of images, each particular one of the echoes being assigned to a different one of the plurality of images.

33. A non-transitory computer-readable medium having stored thereon computer-executable software for performing a method of obtaining information associated with a target, the software comprising:
a first set of instructions capable of configuring a processor to cause a transmission of a plurality of radio-frequency ("RF") pulses toward a target;
a second set of instructions capable of configuring a processor to receive a plurality of echoes associated with each of the pulses, wherein at least one of the echoes reaches a center of k-space at a first point in time and at least further one of the echoes reaches the center of the k-space at a second point in time which is different than the first point; and
a third set of instructions capable of configuring a processor to generate a plurality of images, each particular one of the echoes being assigned to a different one of the plurality of images.

* * * * *